US009616191B2

(12) United States Patent
Van Dijk et al.

(10) Patent No.: US 9,616,191 B2
(45) Date of Patent: Apr. 11, 2017

(54) COMBI-VALVE FOR A BLOWER DRIVEN VENTILATOR

(75) Inventors: Geert Van Dijk, Well (NL); Eugène Herben, Nuenen (NL)

(73) Assignee: Drägerwerk AG & Co. KGaA, Lübeck (DE)

( * ) Notice: Subject to any disclaimer, the term of this patent is extended or adjusted under 35 U.S.C. 154(b) by 1060 days.

(21) Appl. No.: 13/071,891

(22) Filed: Mar. 25, 2011

(65) Prior Publication Data

US 2011/0232640 A1 Sep. 29, 2011

(30) Foreign Application Priority Data

Mar. 26, 2010 (EP) .................................... 10158003

(51) Int. Cl.
*A62B 9/02* (2006.01)
*A61M 16/00* (2006.01)
*A61M 16/20* (2006.01)

(52) U.S. Cl.
CPC ........ *A61M 16/20* (2013.01); *A61M 16/0069* (2014.02); *A61M 16/204* (2014.02); *A61M 16/206* (2014.02)

(58) Field of Classification Search
CPC .... A61M 16/20; A61M 16/208; A61M 16/00; B63C 1/2227; A62B 9/02; G05D 7/0635; F16K 17/10
USPC .......................... 128/200.11–200.24, 203.25, 128/205.13–205.17, 205.24, 207.12, 128/207.16; 137/485–488
See application file for complete search history.

(56) References Cited

U.S. PATENT DOCUMENTS 3,375,839 A * 4/1968 Crenshaw .................... 137/81.1
5,002,050 A 3/1991 McGinnis
6,722,359 B2 4/2004 Chalvignac
6,772,359 B2 8/2004 Kwak et al.
7,195,015 B2 * 3/2007 Kuriyama ................ 128/205.12
2002/0014239 A1 2/2002 Chalvignac
2007/0251527 A1 * 11/2007 Sleeper .................... 128/204.21
2008/0178882 A1 * 7/2008 Christopher et al. .... 128/204.23

FOREIGN PATENT DOCUMENTS

FR 2 887 776 A1 1/2007

* cited by examiner

*Primary Examiner* — Peter S Vasat
*Assistant Examiner* — Ned T Heffner
(74) *Attorney, Agent, or Firm* — McGlew and Tuttle, P.C.

(57) ABSTRACT

A valve assembly for a blower driven ventilator has a first conduit (1), an inlet (2) for receiving fluid from the blower (209) and a first orifice (4). A second conduit (5) is provided with an outlet (6) for forwarding fluid to a patient (203). A membrane (8) includes a front side (9) and a back side (10), wherein at least part of the membrane (8) is movable between a closed position and an open position. A switching circuit (12) enables the selective opening and closing of a fluid connection between the cavity (11) and the blower (209) via the fluid inlet (2), a fluid connection between the cavity (11) and the patient (203) via the fluid outlet (6), and a fluid connection between the cavity (11) and ambient air (13). A control system (17) controls the switching circuit (12) during a ventilation operation of the blower (209).

21 Claims, 5 Drawing Sheets

COMBI-VALVE FOR A BLOWER DRIVEN VENTILATOR

CROSS REFERENCE TO RELATED APPLICATIONS

This application claims the benefit of priority under 35 U.S.C. §119 of European Patent Application EP 10 158 003.3 filed Mar. 26, 2010, the entire contents of which are incorporated herein by reference.

FIELD OF THE INVENTION

The invention relates to a valve assembly for a blower driven ventilator (also known as respirator). The invention further relates to a control system and method for controlling a valve assembly during a ventilation (respiration) operation of a blower.

BACKGROUND OF THE INVENTION

In a mechanical ventilator for providing ventilatory (respiratory) assistance to a patient, different kinds of sources may be used for providing an inspiratory gas mixture to the patient. For example, pressurized air and/or oxygen can be used. Alternatively, a blower can be used. Unlike a pressurized air or oxygen source, the blower has a low pneumatic impedance or resistance when the flow delivery is interrupted. This may typically happen during the patient's expiration. The consequence of the low impedance is that backflow into the ventilator can occur, which can result in rebreathing and airway plateau-pressure drop. The traditional solution to this problem is to design a check-valve (or non-return valve) into the pneumatic system.

In existing systems, controlling the flow generated with a radial blower is difficult, for example it is difficult to control flow for low flow settings, for example for restrictive patients, small children, or any other low compliance patients, or for obstructive patients with high airway resistance. Radial blowers tend to behave oscillatory in case the flow level is controlled, because they may behave as ideal pressure sources at low flow situations. Traditionally this problem is addressed by adding a control valve that acts like a variable resistance, with the radial blower at an almost fixed pressure setting. However, such a valve is rather big because the flow resistance can not be too high relative to the maximum achievable blower pressure. And the power consumption of the blower increases together with the thermal load and noise production.

U.S. Pat. No. 6,722,359 B2 discloses a system with a pneumatic membrane inhalation valve. The front side of the membrane faces an orifice of the airway; the back side can be fluidly connected, via a selector-valve, with either the blower output or the inspiratory conduit, which is connected to the patient via a check-valve. The checkvalve is used to prevent reflow of expiration gases into the blower. That document also discloses a rotary directional-control valve which allows the transmission of the gas stream to be varied by rotating a spool to close or open a passage through an oblong opening.

SUMMARY OF THE INVENTION

It would be advantageous to have an improved valve assembly for a blower driven ventilator. To better address this concern, a first aspect of the invention provides a valve assembly comprising a first conduit comprising an inlet for receiving fluid from the blower and a first orifice; a second conduit comprising an outlet for forwarding fluid to a patient; a membrane comprising a front side and a back side, wherein the back side forms at least part of a boundary of a cavity, and wherein the front side faces the first orifice, and wherein at least part of the membrane is movable in response to a difference in pressure on the front side and the back side of the membrane between a closed position in which the membrane prevents passage of fluid between the first conduit and the second conduit and an open position in which the membrane allows passage of fluid between the first conduit and the second conduit; and a switching circuit for enabling to selectively open and close a fluid connection between the cavity and the blower via the fluid inlet, a fluid connection between the cavity and the patient via the fluid outlet, and a fluid connection between the cavity and ambient air.

Because the cavity can be connected with ambient air, the pressure on the back side can be considerably lowered. This way, the resistance in the circuit is reduced, which allows reducing the pressure drop at the membrane at a higher flow level of gases towards the patient. Moreover, the noise, caused by the blower, may be reduced. Moreover, the energy consumption needed to realize a particular flow level towards the patient may be reduced. The valve may be relatively small compared to a rotary directional-control valve, and still the resistance of the valve may be varied by means of the switching circuit.

Moreover, in case the expiration tubing or valve is obstructed, the patient system can be depressurized by connecting the cavity with ambient air, which enables the expiration gases to flow in the direction of the blower, therewith providing inspiratory pressure relief. Blower overpressure relief may be provided by closing the membrane by connecting the cavity with the fluid inlet. Moreover, the valve assembly may act as a check valve by connecting the cavity with the fluid outlet. The valve assembly may further be used as a variable fluid resistor by connecting it selectively with ambient air or with the fluid outlet. Moreover, by connecting the membrane with the fluid inlet, the flow of fluid from the ventilator to the patient may be stopped altogether. Combining some or all of these functionalities in a single membrane based valve assembly reduces cost and improves efficiency.

The switching circuit may comprise a first switch for selectively connecting the cavity with the fluid outlet or a second switch, and the second switch for selectively connecting the first switch with the fluid inlet or ambient air. This is an efficient implementation of the switching circuit. It allows rapid switching between the fluid inlet and ambient air. Moreover it allows rapid switching to and from the connection with the fluid outlet.

The valve assembly may comprise a control system for controlling the switching circuit during a ventilation operation of the blower. This allows the valve assembly to be given more functionality by setting the switching circuit according to the desired functionality.

The control system may be arranged for connecting the cavity with the fluid outlet during expiration. This way, the membrane will move towards the closed position when expiration pressure is applied. The membrane may act as a check valve during expiration to prevent expired air from reaching the blower.

The control system may be arranged for reducing the blower output pressure to below Positive End-Expiratory Pressure (PEEP) level during expiration. This supports the check valve functionality of the valve assembly.

The control system may be arranged for connecting the cavity with ambient air during pressure controlled ventilation. This setting reduces the resistance caused by the membrane.

The control system may be arranged for connecting the cavity with ambient air or with the fluid outlet during flow controlled ventilation, in dependence on the level of the flow. This allows reducing or increasing the resistance caused by the membrane, which allows the flow to be controlled more accurately. At least some of the problems associated with flow-controlled ventilation may be overcome by varying the resistance using the valve assembly as described herein. Moreover, the blower rotational speed may also be varied in addition to the resistance, to obtain a given flow level.

The control system may be arranged for connecting the cavity with ambient air during flow controlled ventilation for a flow rate above a threshold, and for connecting the cavity with the fluid outlet during flow controlled ventilation for a flow rate below the threshold. This way, for a relatively high volume level, the resistance may be reduced, whereas for a lower volume level, the resistance may be increased.

The control system may be arranged for realizing a particular flow resistance by oscillating between the connection with the fluid outlet and ambient air. By quickly switching between fluid outlet and ambient air, the resistance can be set to a level in between the level corresponding to the connection with fluid outlet and the level corresponding to the connection with ambient air. By adjusting the relative duration of either connection compared to the other, the resistance can be fine-tuned. This allows controlling the flow level with greater accuracy.

The control system may comprise an input for receiving an instruction to provide inspiratory pressure relief, wherein the control system is arranged for connecting the cavity with ambient pressure, and to lower the blower rotational speed, in response to said instruction. By the connection with ambient pressure, while the blower is producing only low or no pressure, the patient can easily exhale, because the air is guided from the patient through the valve towards the blower. The control system may be arranged for setting the blower rotational speed to zero or close to zero.

The control system may comprise an input for receiving a signal indicative of a blower overpressure, and wherein the control system is arranged for connecting the cavity with the fluid inlet when blower overpressure is detected. This connection causes the membrane to move towards the closed position. Consequently, the blower pressure is blocked from the patient, so the blower overpressure is stopped.

The control system may comprise an input for receiving an instruction to perform an occlusion maneuver, and wherein the control system is arranged for connecting the cavity with the fluid inlet during the occlusion maneuver. This connection causes the membrane to move to the closed position, such that the patient cannot breathe.

Another aspect of the invention provides a method of operating the valve assembly set forth, comprising using the membrane as a check valve during expiration to prevent expired air from reaching the blower, by connecting the cavity with the fluid outlet during expiration, and reducing the blower output pressure to below PEEP level during expiration.

Another aspect of the invention provides a method of operating the valve assembly set forth, comprising operating the switching circuit to connect the cavity with ambient air during ventilation, in particular during mandatory inhalation.

It will be appreciated by those skilled in the art that two or more of the above-mentioned embodiments, implementations, and/or aspects of the invention may be combined in any way deemed useful.

These and other aspects of the invention are apparent from and will be elucidated with reference to the embodiments described hereinafter. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
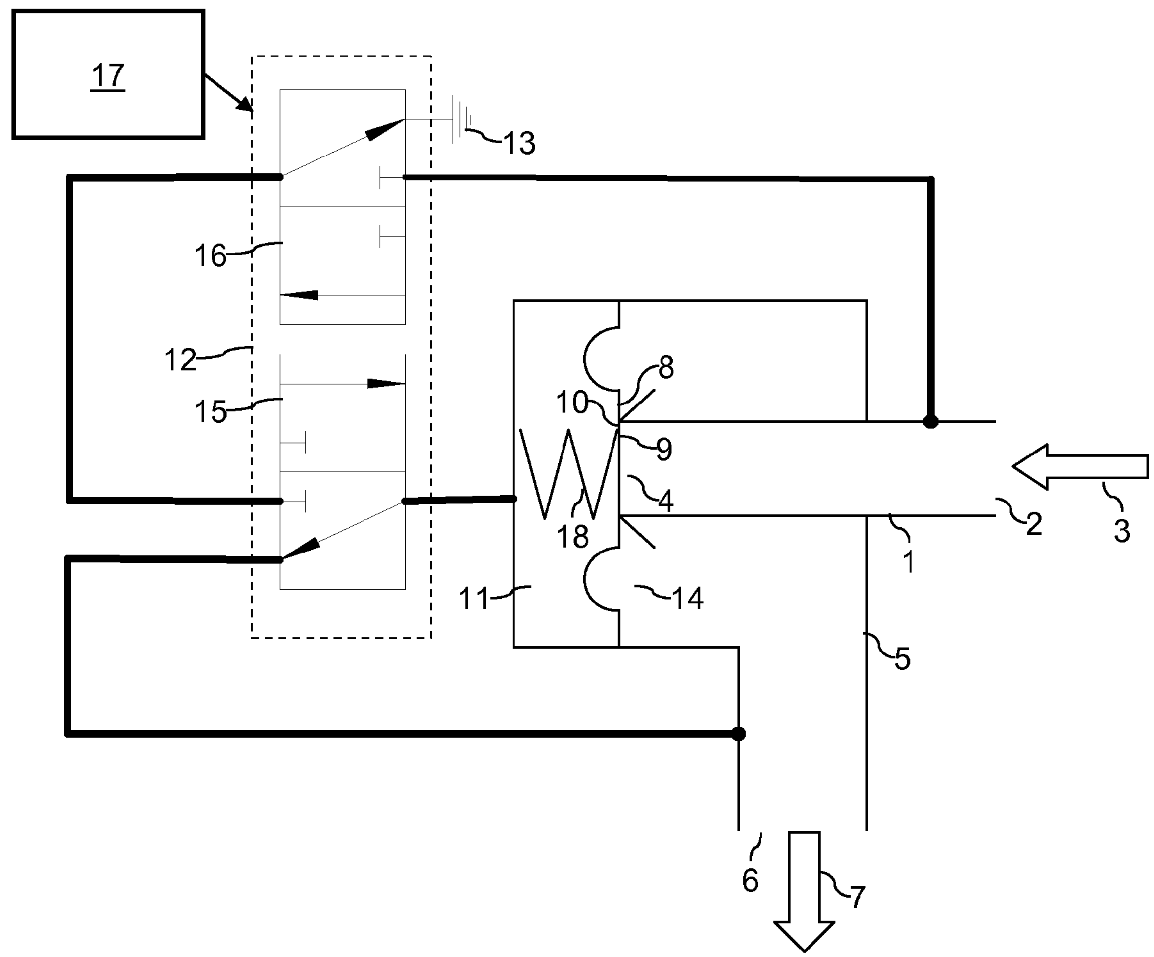
FIG. 1 is a diagram of a valve assembly for a blower driven ventilator.

Referring to the drawings in particular, it is noted that the embodiments described in the following are merely examples. Modifications of these examples may be made by the person skilled in the art.

Figure 2:
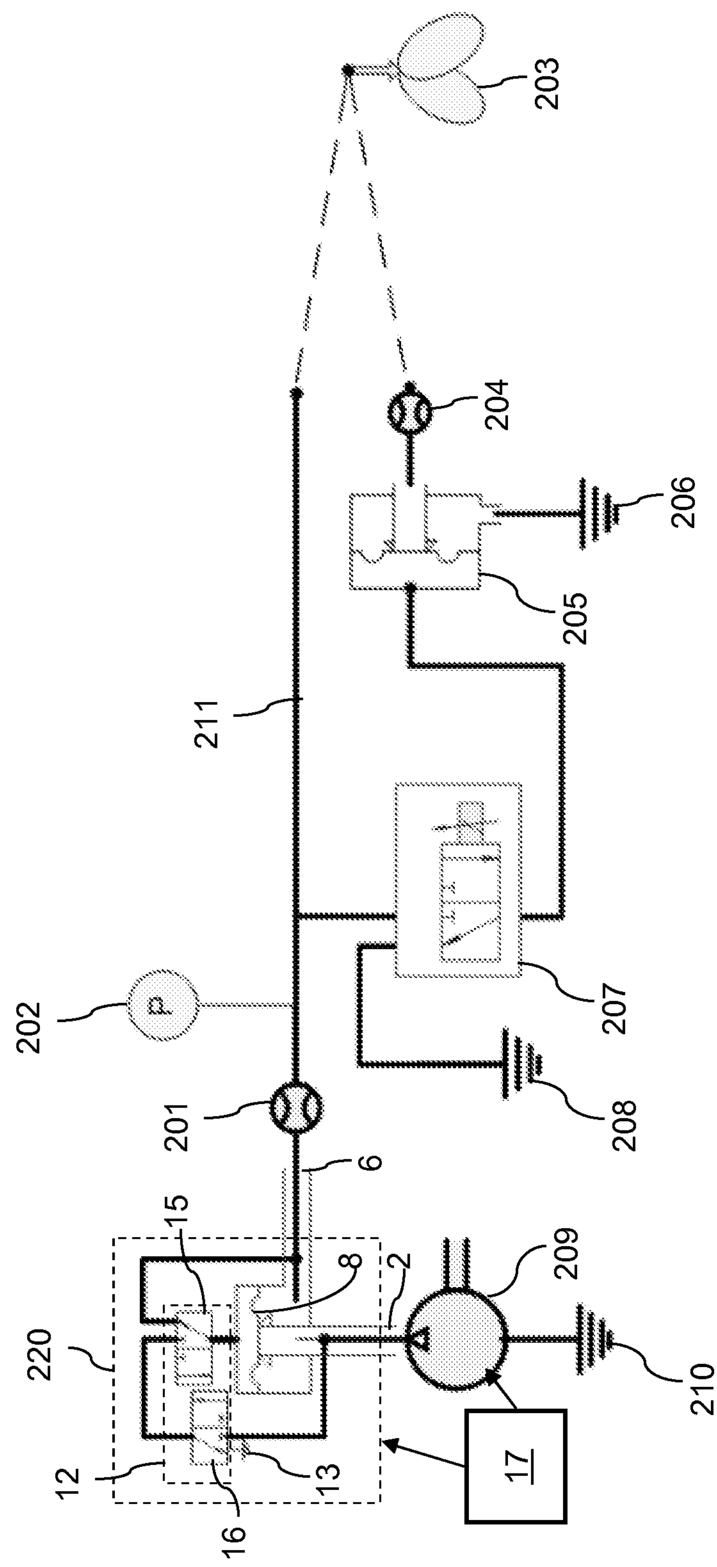
FIG. 2 is a diagram of a patient circuit with a blower.

FIG. 1 shows a diagram of a valve assembly. The valve assembly may be incorporated in a mechanical ventilator, for example a blower driven ventilator. The blower may, for example, comprise a radial blower, as is known in the art per se. Alternatively, the valve assembly may be arranged for being connected with a blower-driven mechanical ventilator. FIG. 2 shows a diagram of a patient circuit comprising the valve assembly 220 of FIG. 1. In the figures, similar items have been given the same reference numerals.

The valve assembly 220, as illustrated in FIGS. 1 and 2, comprises a first conduit 1 for transporting fluid from a blower 209 to an orifice 4. This orifice 4 is referred to hereinafter as the first orifice 4. The fluid from the blower 209 arrives at an inlet 2 of the conduit 1, as indicated by arrow 3.

The valve assembly may further comprise a second conduit 5. This second conduit may comprise an outlet 6 for forwarding fluid to a patient 203, as indicated by arrow 7.

The flow from the inlet 2 to the outlet 6 via the first conduit 1 and the second conduit 5 may be controlled by means of a membrane 8 comprising a front side 9 and a back side 10. The back side 10 may form at least part of an inner boundary of a cavity 11. By varying the pressure in this cavity 11, the flow may be controlled. The front side 9 may face the first orifice 4. At least part of the membrane 8 is movable in response to a difference in pressure on the front side 9 and the back side 10 of the membrane 8. The membrane 8 may move or deform into a closed position, as illustrated, in which the membrane 8 closes the first orifice 4. In the closed position, the membrane 8 prevents passage of fluid between the first conduit 1 and the second conduit 5. The membrane may also move or deform into an open position, in which the first orifice 4 is opened. In the open position, passage of fluid between the first conduit 1 and the second conduit 5 is enabled. A bias 18 may be provided, for example in form of a spring, to favor the closed position. The bias may also be provided by an elasticity of the membrane in combination with the way in which it is attached in the valve assembly with respect to the border of the first orifice 4 and/or second orifice 14. However, this bias is optional.

The valve assembly may further comprise a switching circuit 12. The switching circuit 12 enables the selective opening and closing of a fluid connection between the cavity 11 and at least one of:

- the blower 209. This fluid connection may be realized via the first conduit 1 and the fluid inlet 2;
- the patient 203. This fluid connection may be realized via the second conduit 5 and the fluid outlet 6; and
- ambient air 13.

The second conduit 5 may comprise a second orifice 14. This second orifice 14 may be arranged adjacent the first orifice 4, such that a portion of the front side 9 of the membrane 8 faces the second orifice 14. In the closed position, the membrane 8 may prevent passage of fluid between the first orifice 4 and the second orifice 14. In the open position, the membrane 8 may allow passage of fluid between the first orifice 4 and the second orifice 14.

The figures show an example implementation of the switching circuit using two switches. However, this is only an example. Another implementation could use a single switch having three positions, for example. In the example implementation, the switching circuit 12 comprises a first switch 15 for selectively connecting the cavity 11 with the fluid outlet 6 or a second switch 16. The second switch 16 selectively connects the first switch 15 with the fluid inlet 2 or ambient air 13. Consequently, when the first switch 15 connects to the second switch 16, the second switch connects the cavity 11 with the fluid inlet 2 or ambient air 13.

The valve assembly may comprise a control system 17 for controlling the switching circuit 12. During a ventilation operation of the blower 209, the control system 17 may change the connection of the cavity 11 to regulate the flow of gases to and from the patient and/or the blower. The control system may further control operation of the blower 209. However, the blower 209 and the switching circuit 12 may also be controlled by separate controllers. Such separate controllers may be synchronized to obtain an effective control of the membrane 8 and the blower 209 during inhalation and exhalation.

The control system 17 may control the switching circuit in a number of ways to obtain different functionality by means of the valve assembly 220.

For example, the control system 17 may be arranged for connecting the cavity 11 with the fluid outlet 6 during expiration. This way, the membrane 8 is kept in the closed position, for example because of the optional bias 18 or because the back side 10 of the membrane 8 is larger than the portion of the front side 9 facing the second orifice 14. The control system may further control the blower to generate a suitably low pressure. For example, by reducing the blower output pressure to below PEEP level during expiration. Herein, PEEP means positive end-expiratory pressure. Positive end-expiratory pressure (PEEP) is a term used in mechanical ventilation to denote the amount of pressure present in the airway at the end of the expiratory cycle. Effectively, this way the membrane 8 may help preventing expired air from reaching the blower (209). The membrane 8 may thus act as a check valve during expiration.

The control system 17 may be arranged for connecting the cavity 11 with ambient air 13 during pressure controlled ventilation. The connection with ambient air 13 causes the resistance of the membrane to be reduced. Consequently, it is easier to control the pressure by controlling the pressure generated by the blower.

The control system 17 may be arranged for connecting the cavity 11 with ambient air 13 or with the fluid outlet 6 during flow controlled ventilation, in dependence on the level of the flow. Controlling the flow generated with a blower is easier when the resistance can be varied. One way of varying the resistance of the patient circuit is by connecting the cavity with ambient air 13 or with the fluid outlet 6. The latter causes a larger resistance than the former. For example, the control system 17 may be arranged for connecting the cavity 11 with ambient air 13 during flow controlled ventilation for a flow rate above a threshold, and for connecting the cavity 11 with the fluid outlet 6 during flow controlled ventilation for a flow rate below the threshold. At the same time the rotation speed of the blower may be adapted to the resistance to provide the desired flow rate.

Alternatively, the control system 17 may be arranged for realizing a particular flow resistance by oscillating between the connection with the fluid outlet 6 and ambient air 13. By oscillating between these two positions, a pressure in between ambient pressure and fluid outlet pressure may be realized in the cavity. By controlling the relative duration of both connections, a variable resistance may be obtained.

The control system 17 may comprise an input for receiving an instruction. This input is not shown in the drawing. The input may comprise a user interface element on the ventilator. For example, a button may be provided or the instruction may be given by means of a touch screen. Alternatively, the input is arranged for receiving an automatically generated signal from a measurement device. Such measurement device may be arranged for providing an alarm signal in suitable cases. The control system 17 may be arranged for responding to such automatic signal by changing the settings of the switching circuit and/or the blower, to remove the alarm condition. This way, a fault in the system may be overcome without adverse effect on the patient.

For example, an instruction to provide inspiratory pressure relief may be received by the control system 17 via the input. The control system 17 may be arranged for connecting the cavity with ambient pressure 13, and to lower a blower rotational speed, in response to said instruction. This way, inspiratory pressure is lowered significantly.

In another example, a signal indicative of a blower overpressure, or an instruction to provide blower overpressure relief, may be received by the control system 17. The control system 17 may be arranged for connecting the cavity 11 with the fluid inlet 2 in response thereto. By providing this connection, the membrane 6 moves into the closed position, therewith removing the pressure caused by the blower.

In another example, the input is arranged for receiving an instruction to perform an occlusion maneuver. In response to this instruction, the control system 17 may be arranged for connecting the cavity 11 with the fluid inlet 2 during the occlusion maneuver. This way, the membrane 8 may be kept in the closed position, in particular when the blower 209 provides sufficient pressure.

The valve assembly may be implemented as an integral part of a mechanical ventilator comprising a blower 209.

FIG. 2 illustrates how the valve assembly may be integrated in the ventilator and/or patient circuit. A flow sensor 201 and pressure sensor 202 may be provided in between the valve assembly 220 and the patient 203. The expiratory circuit may comprise a flow sensor 204, a membrane based valve 205, and a proportional control valve (or switch) 207. When the membrane based valve 205 is open, the expiratory gases may be released into ambient environment 206. When the membrane based valve 205 is closed, expiratory gases may not normally be released, in order to obtain sufficient inspiratory pressure. A proportional control valve 207 may be used to connect the back side of the membrane based valve 205 with the inspiratory conduit 211 or with ambient air 208, in order to close or open the membrane based valve 205, respectively.

It is noted that a check valve in the inspiratory conduits between the blower 209 and the patient 203 does not need to be in place, because this functionality can be obtained by means of the valve assembly 220, for example using the control system 17.

A method of operating the valve assembly 220, for example by control system 17, comprises using the membrane 8 as a check valve during expiration to prevent expired air from reaching the blower 209. The method may comprise connecting the cavity 11 with the fluid outlet 6 during expiration, and reducing the blower output pressure to below PEEP level during expiration.

Another method of operating the valve assembly 220 comprises connecting the cavity 11 with ambient air 13 for reducing the resistance caused by the membrane 8, for example during inspiration.

These methods may be implemented in software as a computer program product. Also other functionality of the control system 17 described herein may be implemented at least partly in software. This software may be executed by a microprocessor of the ventilator. Other ways of implementing the methods and functions are also possible.

In an embodiment, the valve consists of a pneumatic part with a spring loaded membrane and two bistable 3/2 pilot valves. With the pneumatic arrangement as drawn in FIG. 1, it may be possible to set three pressure levels at the back side 10 of the membrane 8. Either ambient pressure, fluid inlet pressure (pressure generated by the blower 209) or fluid outlet pressure (pressure at the outlet 6 of the valve assembly, towards the patient).

In case of pressure controlled ventilation, it may be advantageous to have a low inspiratory resistance. The membrane 8 may be made to have the maximum clearance relative to the first orifice 4, drawn as a crater (valve seat) in the figure. The membrane can be lifted to the maximum by setting the backpressure to ambient pressure. The blower pressure may easily lift the membrane. To this end, control valve or switch 16 may be switched to the ambient pressure 13 inlet port and control valve or switch 15 may be switched to the inlet port of control valve or switch 16.

If the control valves would remain in this state during expiration, rebreathing might occur. However if control valve or switch 15 is switched to the valve outlet 6 pressure and the blower reduces the pressure to near or below PEEP level, the membrane closes and there rebreathing may be avoided.

In case of flow controlled ventilation, the objective may be to have an appropriate inspiratory resistance for low flow and/or for high flow, as desired. For higher flow levels, the maximum open membrane valve may be used, by connecting the cavity 11 to ambient air 13. Increasing the resistance might reduce the performance and might reduce energy efficiency and/or noise comfort. To increase the resistance of the valve (for lower flow levels), control valve or switch 15 may be set to the outlet 6 pressure of the valve assembly 220. The valve then still opens when the blower pressure is sufficiently high. When going to expiration the valve automatically closes at unchanged control valve settings.

At higher flow values this increased resistance may be less desirable. Therefore, above a specific flow level, the valve resistance may be decreased by switching control valve or switch 15 back to the inlet pressure of control valve 16, which is set open to ambient.

This covers a number of normal ventilation modes. The system may also be used to overcome several fault conditions. For example, to provide inspiratory pressure relief, control valve 15 may be switched to the outlet of control valve 16 which may be switched to ambient pressure. The membrane 8 valve opens. To provide blower overpressure relief, control valve 15 may be switched to the outlet of control valve 16 which may be switched to the outlet blower pressure. Because of the arrangement of the membrane 8, for example using appropriate valve ratio and/or a small bias, e.g. a spring load, the membrane closes directly.

The system may also be used to perform an occlusion maneuver. In this case, control valve 15 may be switched to the outlet of control valve 16 which may be switched to the outlet blower pressure. This may be done for the prescribed occlusion time (for example, 100 milliseconds).

In an embodiment, the control valve may be integrated into a manifold or blower housing. The control valves or switches may be mounted directly outside of the manifold (or at another suitable position) and interconnected through tubing (not shown in the drawings).

Figure 3:
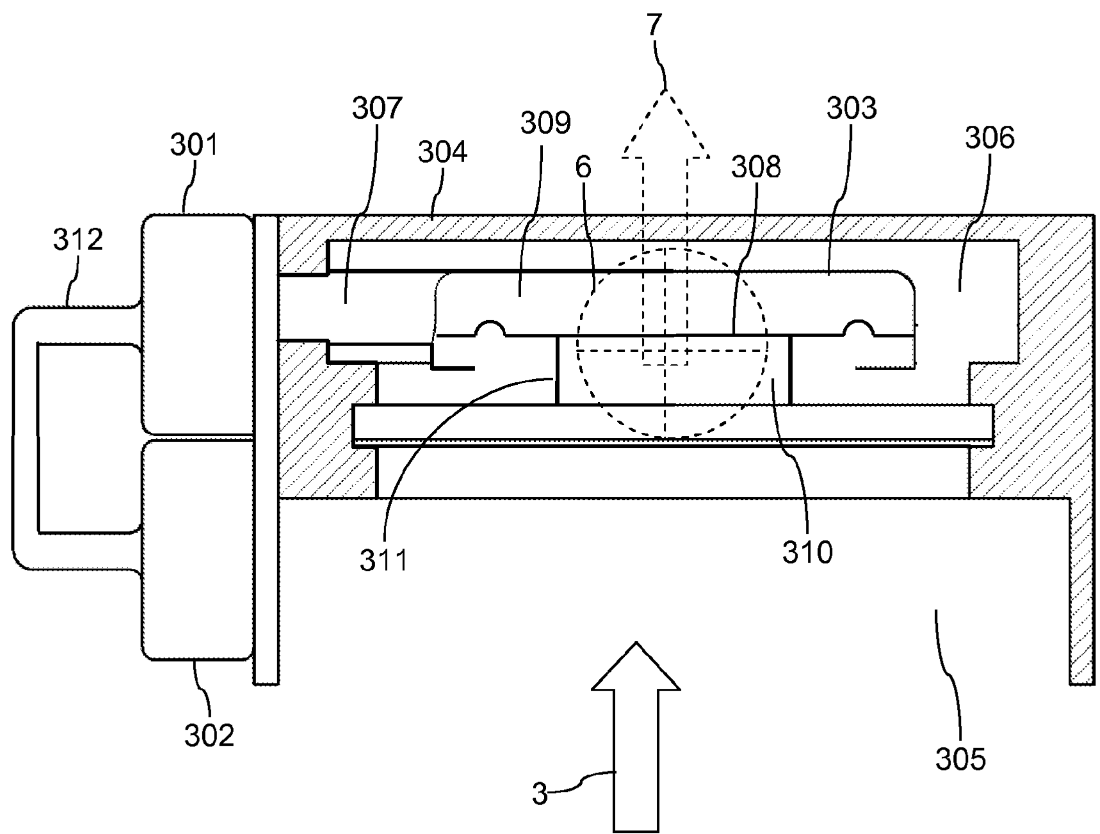
FIG. 3 is a side view of a valve assembly.
Figure 4:
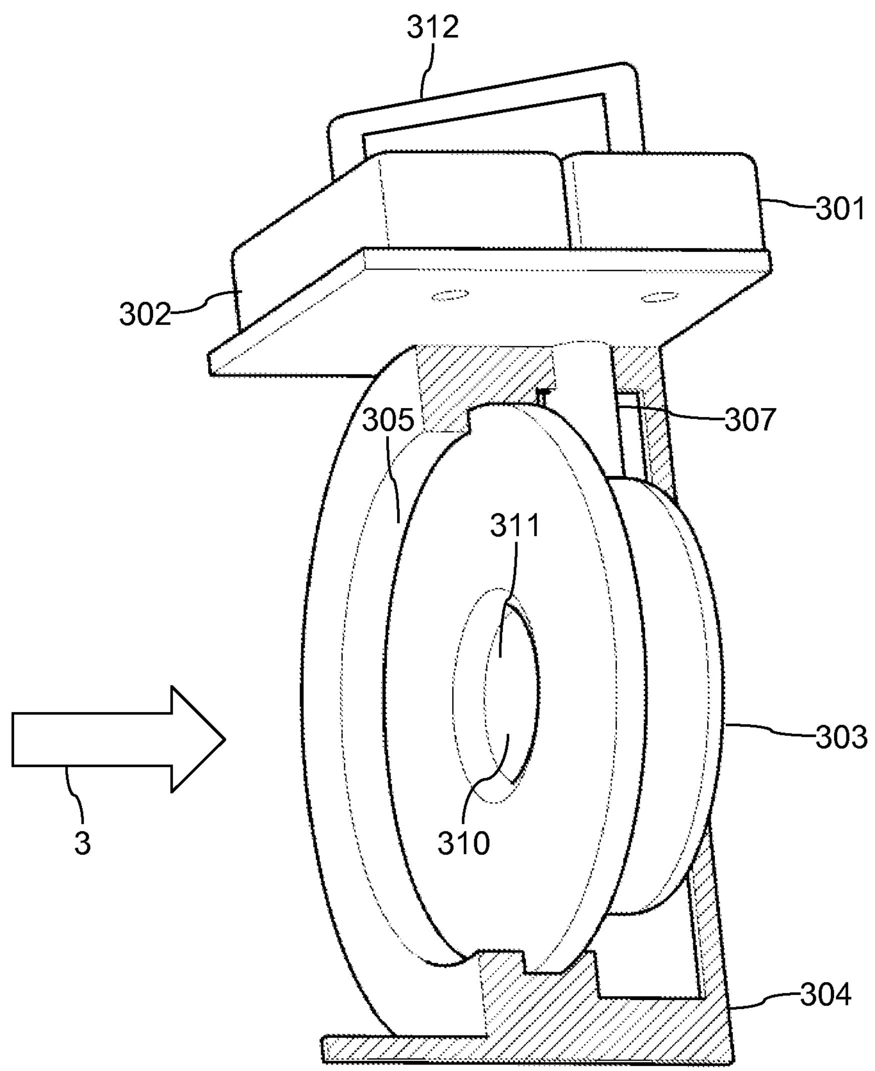
FIG. 4 is an oblique view of front side of a valve assembly.
Figure 5:
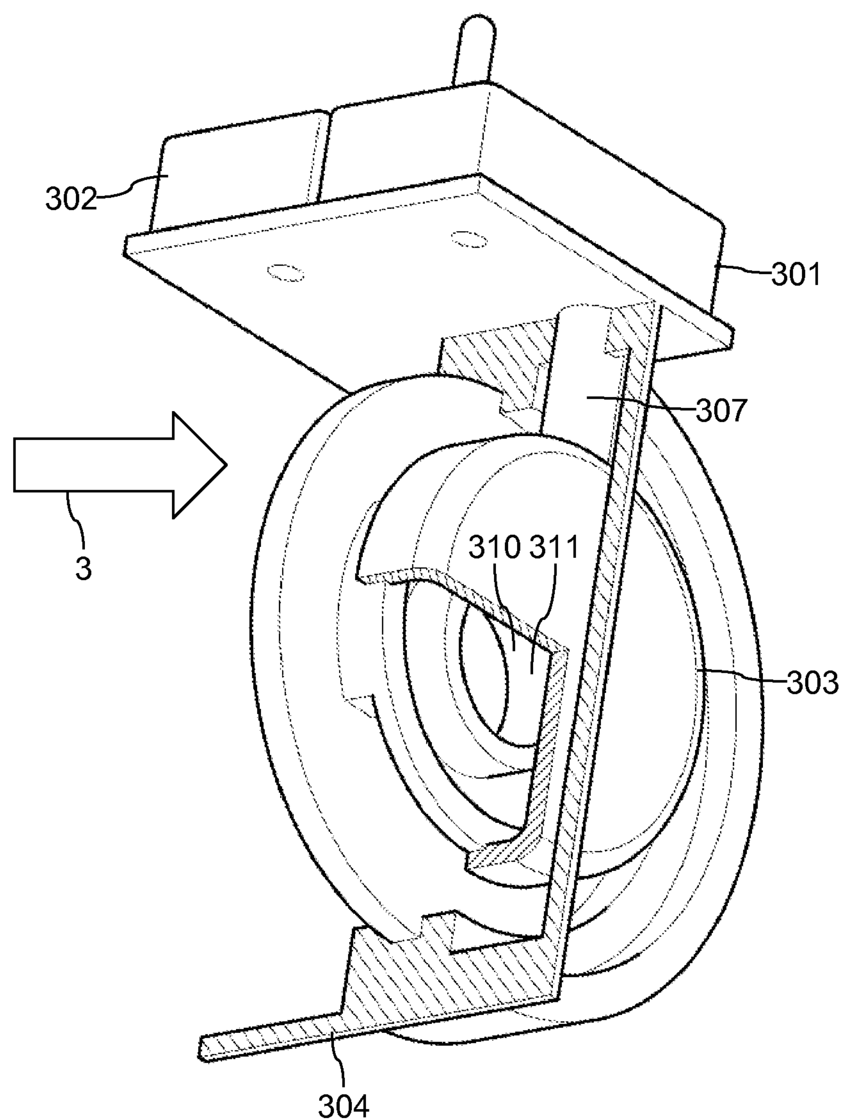
FIG. 5 is an oblique view of a back side of a valve assembly.

FIGS. 3, 4, and 5 illustrate an example embodiment of the valve assembly as described herein. FIG. 3 shows a side view with intersected view of the housing 304. FIG. 4 shows an oblique frontal view with intersected view of the housing 304. FIG. 5 shows an oblique rear view with intersected view of the housing 304 and membrane valve 303. Similar items have been indicated with the same reference numerals. The figures show two switches, in this case piezo valves 301 and 302, a membrane valve 303, and a housing 304. The piezo valves may be obtained from Hoerbiger, Germany, for example. Membrane valve 303 comprises a membrane 308 with a crater 311 on a front side of the membrane 308 and a cavity 309 on a back side of the membrane 308. The membrane 308 may be biased towards the crater 311 (not shown). First conduit 305, 310 may be connected to the blower output (not shown). The first conduit 305 extends at 310 in the crater 311 so that air 3 from the blower reaches the membrane 308. Arrow 3 indicates the direction of flow from the blower into the first conduit 305, 310. Second conduit 306 has an outlet 6 (sketched as a dashed circle) to enable air to leave the conduit 306 in the direction of arrow 7. A patient hose may be connectable to the second conduit 306 to transport the air to a patient (not shown). Piezo valve 301 is connected to the cavity 309 on the back side of the membrane 308 via conduit 307. Depending on the position of piezo valve 301, the cavity is connected with the second conduit 306 or, via conduit 312, with piezo valve 302. Piezo valve 302 may, depending on its position, connect the outlet of the piezo valve 301 with either of ambient air or the first conduit 305.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

While specific embodiments of the invention have been shown and described in detail to illustrate the application of the principles of the invention, it will be understood that the invention may be embodied otherwise without departing from such principles.

What is claimed is:

1. A valve assembly for a blower driven ventilator, the valve assembly comprising:

a first conduit comprising a fluid inlet for receiving fluid from a blower of the blower driven ventilator and a first orifice;

a second conduit comprising a patient fluid outlet for forwarding fluid to a patient;

a membrane valve operable in different operation modes, the membrane valve comprising a cavity and a membrane comprising a front side and a back side, wherein the back side forms at least part of a boundary of the cavity, wherein at least part of the membrane is movable, in response to a difference in pressure on the front side and the back side of the membrane, between a closed position in which the membrane prevents passage of fluid between the first conduit and the second conduit and an open position in which the membrane allows passage of fluid between the first conduit and the second conduit;

a switching circuit having a plurality of switching states to change the operation modes of the membrane valve;

a fluid connection between the switching circuit and the cavity;

a fluid connection between the switching circuit and the blower via the fluid inlet;

a fluid connection between the switching circuit and the patient via the fluid outlet; and a fluid connection between the switching circuit and ambient air, the switching circuit enabling a selective opening and closing of a fluid connection between the cavity and the blower via the fluid inlet to switch the membrane valve to a blower pressure operation mode with the fluid connection between the cavity and the fluid inlet open, enabling a selective opening and closing of a fluid connection between the cavity and the patient via the fluid outlet to switch the membrane valve to a patient outlet pressure operation mode with the fluid connection between the cavity and the patient fluid outlet open, and enabling a selective opening and closing of a fluid connection between the cavity and ambient air to switch the membrane valve to an ambient air pressure operation mode with the fluid connection between the cavity and ambient air open.

2. A valve assembly according to claim 1, wherein the cavity is formed with the fluid connection to the switching circuit such that fluid pressure in the cavity is based on a fluid pressure of the fluid inlet in the blower pressure operation mode, with the fluid connection between the cavity and the blower via the fluid inlet, such that fluid pressure in the cavity is based on a fluid pressure of the fluid outlet in the patient outlet pressure operation mode, with the fluid connection between the cavity and the patient via the fluid outlet, and such that fluid pressure in the cavity is based on a fluid pressure of ambient air in the ambient air pressure operation mode, with the fluid connection between the cavity and ambient air.

3. A valve assembly according to claim 1, further comprising a control system for controlling the switching state of the switching circuit to switch the membrane valve between two or more of the blower pressure operation mode, the patient outlet pressure operation mode and the ambient air pressure operation mode during a ventilation operation of the blower.

4. A valve assembly according to claim 3, wherein the control system controls the switching circuit to switch the membrane valve to the ambient air pressure operation mode to connect the cavity with ambient air during pressure controlled ventilation.

5. A valve assembly according to claim 3, wherein the control system comprises an input for receiving an instruction to provide inspiratory pressure relief, and wherein the control system controls the switching circuit to switch the membrane valve to the ambient air pressure operation mod for connecting the cavity with ambient pressure and controls the blower to lower a blower rotational speed, in response to the instruction.

6. A valve assembly according to claim 3, wherein the control system comprises an input for receiving a signal indicative of a blower overpressure, and wherein the control system controls the switching circuit to switch the membrane valve to a blower pressure operation mode to connect the cavity with the fluid inlet when a blower overpressure is detected.

7. A valve assembly according to claim 3, wherein the control system comprises an input for receiving an instruction to perform an occlusion maneuver, and wherein the control system controls the switching circuit to switch the membrane valve to a blower pressure operation mode for connecting the cavity with the fluid inlet during the occlusion maneuver.

8. A valve assembly according to claim 3, wherein the control system controls the switching state of the switching circuit to switch the membrane valve to the patient outlet pressure operation mode to connect the cavity with the fluid outlet during expiration.

9. A valve assembly according to claim 8, wherein the control system reduces a blower output pressure to below PEEP level during expiration.

10. A valve assembly according to claim 9, wherein with the membrane valve acts as a check valve during expiration to prevent expired air from reaching the blower.

11. A valve assembly according to claim 3, wherein the control system controls the switching circuit to switch the membrane valve to the ambient air pressure operation mode to connect the cavity with ambient air or to switch the membrane valve to the patient outlet pressure operation mode to connect the cavity with the fluid outlet during flow controlled ventilation, in dependence on a level of flow.

12. A valve assembly according to claim 11, wherein the control system controls the switching circuit to switch the membrane valve to the ambient air pressure operation mode to connect the cavity with ambient air during flow controlled ventilation for a flow rate above a threshold, and to switch the membrane valve to the patient outlet pressure operation mode to connect the cavity with the fluid outlet during flow controlled ventilation for a flow rate below the threshold.

13. A valve assembly according to claim 11, wherein the control system controls the switching circuit for realizing a particular flow resistance by oscillating between switching the membrane valve to the patient outlet pressure operation mode with the connection with the fluid outlet and switching the membrane valve to the ambient air pressure operation mode with the connection with the ambient air.

14. A mechanical ventilator comprising:
- a blower; and
- a valve assembly comprising:
  - a first conduit comprising a fluid inlet for receiving fluid from a blower of the blower driven ventilator and a first orifice;
  - a second conduit comprising a fluid outlet for forwarding fluid to a patient;
  - a membrane valve operable in different operation modes, the membrane valve comprising a boundary defining a fluid volume and a membrane comprising a front side and a back side, wherein the back side forms at least part of the boundary of the fluid volume, wherein at least part of the membrane is movable, in response to a difference in pressure on the front side and the back side of the membrane, between a closed position in which the membrane prevents passage of fluid between the first conduit and the second conduit and an open position in which the membrane allows passage of fluid between the first conduit and the second conduit;
  - a switching circuit having a plurality of switching states to change the operation modes of the membrane valve;
  - a fluid connection between the switching circuit and the fluid volume;
  - a fluid connection between the switching circuit and the blower via the fluid inlet;
  - a fluid connection between the switching circuit and the patient via the fluid outlet; and
  - a fluid connection between the switching circuit and ambient air, the switching circuit selectively opening and closing a fluid connection between the fluid volume and the blower via the fluid inlet to switch the membrane valve to a blower pressure operation mode with the fluid connection between the cavity and the fluid inlet open, selectively opening and closing a fluid connection between the fluid volume and the patient via the fluid outlet to switch the membrane valve to a patient outlet pressure operation mode with the fluid connection between the cavity and the patient fluid outlet open, and selectively opening and closing a fluid connection between the fluid volume and ambient air to switch the membrane valve to an ambient air pressure operation mode with the fluid connection between the cavity and ambient air open.

15. A mechanical ventilator according to claim 14, further comprising a control system for controlling the switching state of the switching circuit to switch the membrane valve between two or more of the blower pressure operation mode, the patient outlet pressure operation mode and the ambient air pressure operation mode during a ventilation operation of the blower.

16. A mechanical ventilator according to claim 15, wherein the control system is connected to the blower for controlling a blower output pressure of the blower.

17. A mechanical ventilator according to claim 16, further comprising:
- a computer program product comprising instructions for the control system controlling the switching circuit during a ventilation operation of the blower.

18. A method of operating a valve assembly, the method comprising the steps of:
- providing a blower driven ventilator with a valve assembly comprising:
  - a first conduit comprising a fluid inlet for receiving fluid from a blower of the blower driven ventilator and a first orifice;
  - a second conduit comprising a fluid outlet for forwarding fluid to a patient;
  - a membrane valve operable in different operation modes, the membrane valve comprising a fluid volume and a membrane comprising a front side and a back side, wherein the back side forms at least part of a boundary of the fluid volume, wherein at least part of the membrane is movable, in response to a difference in pressure on the front side and the back side of the membrane, between a closed position in which the membrane prevents passage of fluid between the first conduit and the second conduit and an open position in which the membrane allows passage of fluid between the first conduit and the second conduit;
  - a switching circuit having a plurality of switching states to change the operation modes of the membrane valve;
  - a fluid connection between the switching circuit and the fluid volume;
  - a fluid connection between the switching circuit and the blower via the fluid inlet;
  - a fluid connection between the switching circuit and the patient via the fluid outlet; and
  - a fluid connection between the switching circuit and ambient air, the switching circuit selectively opening and closing a fluid connection between the fluid volume and the blower via the fluid inlet to switch the membrane valve to a blower pressure operation mode with the fluid connection between the cavity and the fluid inlet open, selectively opening and closing a fluid connection between the fluid volume and the patient via the fluid outlet to switch the membrane valve to a patient outlet pressure operation mode with the fluid connection between the cavity and the patient fluid outlet open, and selectively opening and closing a fluid connection between the fluid volume and ambient air to switch the membrane valve to an ambient air pressure operation mode with the fluid connection between the cavity and ambient air open; and
- operating the switching circuit to change the operation mode of the membrane valve.

19. A method according to claim 18, further comprising the step of:
- providing a control system connected to the blower for controlling the blower output pressure and connected to the switching circuit for controlling the switching state of the switching circuit; and
- controlling the switching circuit to switch the membrane valve between two or more of the blower pressure operation mode, the patient outlet pressure operation mode and the ambient air pressure operation mode during a ventilation operation of the blower.

20. A method according to claim 19, further comprising the step of:
- using the membrane valve as a check valve during expiration to prevent expired air from reaching the blower, by connecting the fluid volume with the fluid outlet during expiration, and reducing the blower output pressure to below PEEP level during expiration.

21. A method according to claim 19, further comprising the step of:

providing a computer program product comprising instructions for the control system controlling the switching circuit during a ventilation operation of the blower.

* * * * *